US010624592B2

(12) United States Patent
Sakaguchi et al.

(10) Patent No.: US 10,624,592 B2
(45) Date of Patent: Apr. 21, 2020

(54) X-RAY DIAGNOSIS APPARATUS AND ARM CONTROL METHOD

(71) Applicant: TOSHIBA MEDICAL SYSTEMS CORPORATION, Otawara-Shi (JP)

(72) Inventors: Takuya Sakaguchi, Utsunomiya (JP); Ko Fuchigami, Otawara (JP); Shinichi Hashimoto, Otawara (JP); Hiroyuki Ohuchi, Otawara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 521 days.

(21) Appl. No.: 14/640,811

(22) Filed: Mar. 6, 2015

(65) Prior Publication Data
US 2015/0173693 A1 Jun. 25, 2015

Related U.S. Application Data

(63) Continuation of application No. PCT/JP2013/075586, filed on Sep. 20, 2013.

(30) Foreign Application Priority Data

Sep. 20, 2012 (JP) .................. 2012-207497

(51) Int. Cl.
A61B 6/08 (2006.01)
A61B 8/00 (2006.01)
(Continued)

(52) U.S. Cl.
CPC .............. A61B 6/08 (2013.01); A61B 6/06 (2013.01); A61B 6/4441 (2013.01); A61B 6/463 (2013.01);
(Continued)

(58) Field of Classification Search
CPC .. A61B 6/032; A61B 6/08; A61B 6/12; A61B 6/4441; A61B 6/463; A61B 6/466;
(Continued)

(56) References Cited

U.S. PATENT DOCUMENTS 5,159,622 A 10/1992 Sakaniwa et al.
6,775,404 B1 * 8/2004 Pagoulatos ............... G06T 3/00
128/916
(Continued)

FOREIGN PATENT DOCUMENTS

JP 03-158139 A 7/1991
JP 2002-136507 A 5/2002
(Continued)

OTHER PUBLICATIONS

International Search Report dated Oct. 29, 2013 for PCT/JP2013/075586 filed on Sep. 20, 2013 with English Translation.
International Written Opinion dated Oct. 29, 2013 for PCT/JP2013/075586 filed on Sep. 20, 2013.

Primary Examiner — Boniface N Nganga
(74) Attorney, Agent, or Firm — Oblon, McClelland, Maier & Neustadt, L.L.P.

(57) ABSTRACT

An X-ray diagnosis apparatus according to an embodiment includes a calculating unit and a control unit. The calculating unit that calculates an angle between a specified position specified in an ultrasonic image generated through transmission and reception of ultrasonic waves by an ultrasound probe and a predetermined position in a radiographic space where a subject is radiographed based on information on a relative position between the radiographic space and a scanning space where the subject is scanned by the ultrasound probe. The control unit that controls an arm to move so that the subject is radiographed at the angle calculated by the calculating unit.

12 Claims, 14 Drawing Sheets

(51) Int. Cl.
*A61B 6/00* (2006.01)
*A61B 8/13* (2006.01)
*A61B 6/03* (2006.01)
*A61B 8/08* (2006.01)
*A61B 6/06* (2006.01)
*A61B 6/12* (2006.01)

(52) U.S. Cl.
CPC .............. *A61B 6/466* (2013.01); *A61B 6/503* (2013.01); *A61B 6/5247* (2013.01); *A61B 6/54* (2013.01); *A61B 8/0883* (2013.01); *A61B 8/13* (2013.01); *A61B 8/42* (2013.01); *A61B 8/4245* (2013.01); *A61B 8/4416* (2013.01); *A61B 8/463* (2013.01); *A61B 8/466* (2013.01); *A61B 8/485* (2013.01); *A61B 8/5261* (2013.01); *A61B 8/54* (2013.01); *A61B 6/032* (2013.01); *A61B 6/12* (2013.01)

(58) Field of Classification Search
CPC ......... A61B 6/503; A61B 6/5247; A61B 6/54; A61B 8/0883; A61B 8/13; A61B 8/42; A61B 8/4245; A61B 8/4416; A61B 8/463; A61B 8/466; A61B 8/485; A61B 8/5261; A61B 8/54; A61B 6/06
See application file for complete search history.

(56) References Cited

U.S. PATENT DOCUMENTS

| | | | |
|---|---|---|---|
| 7,845,851 B2 | 12/2010 | Rasche | |
| 9,901,320 B2* | 2/2018 | DeFreitas | A61B 8/0825 |
| 2002/0090058 A1 | 7/2002 | Yasuda et al. | |
| 2006/0215817 A1* | 9/2006 | Watanabe | A61B 6/4441 |
| | | | 378/114 |
| 2007/0276243 A1* | 11/2007 | Gerard | A61B 6/12 |
| | | | 600/440 |
| 2008/0234570 A1* | 9/2008 | Gerard | A61B 6/12 |
| | | | 600/424 |
| 2009/0043200 A1 | 2/2009 | Abe | |
| 2010/0111389 A1* | 5/2010 | Strobel | A61B 6/12 |
| | | | 382/131 |
| 2010/0215150 A1* | 8/2010 | Vallee | A61B 6/12 |
| | | | 378/98.12 |
| 2015/0182191 A1* | 7/2015 | Caluser | A61B 8/5246 |
| | | | 600/440 |

FOREIGN PATENT DOCUMENTS

| | | |
|---|---|---|
| JP | 2004-329729 A | 11/2004 |
| JP | 2009-039429 A | 2/2009 |
| JP | 2009-507600 A | 2/2009 |
| JP | 2010-162058 A | 7/2010 |
| JP | 2012-152519 A | 8/2012 |

* cited by examiner

FIG.10
(A)
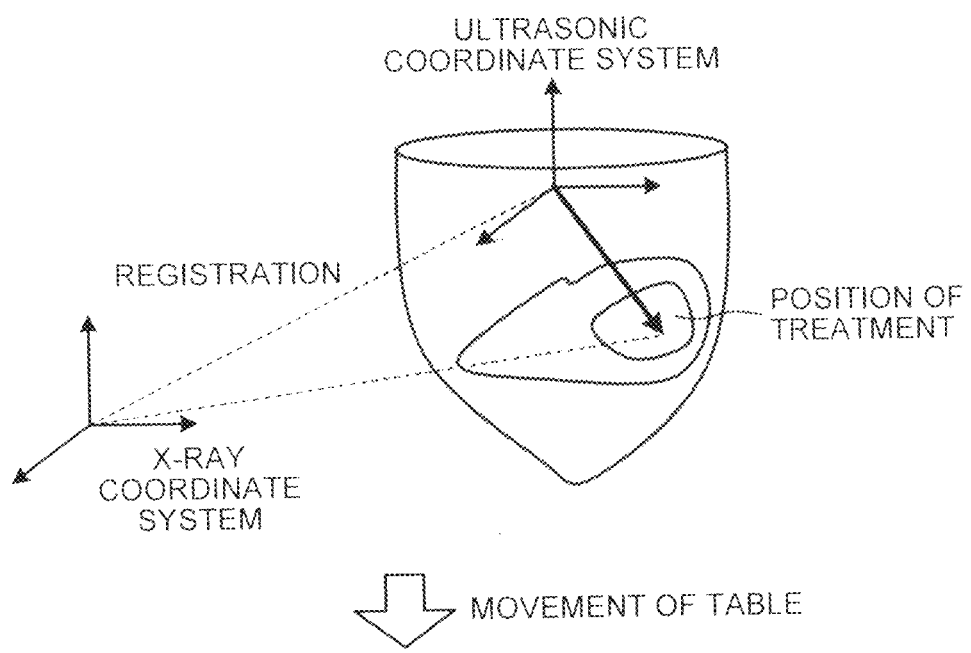
(B)
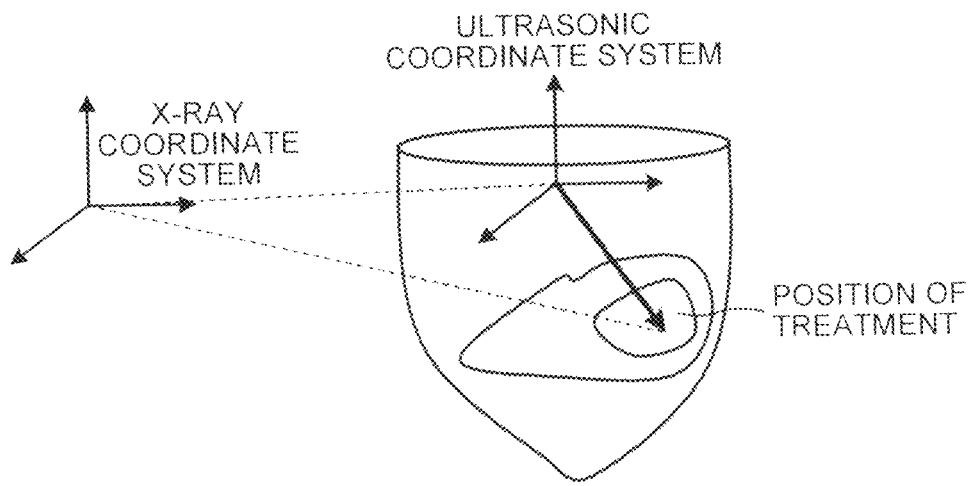

FIG.12
(A)
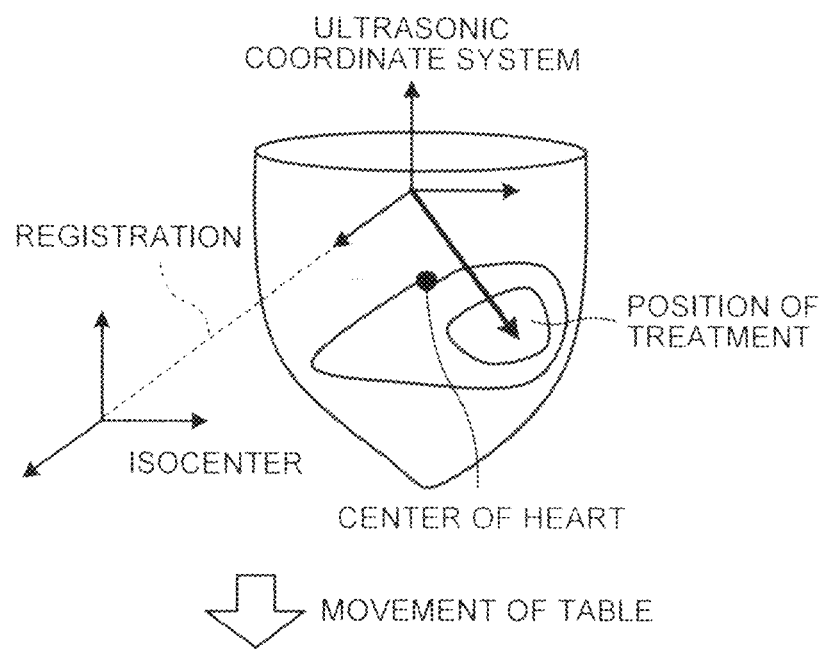
(B)
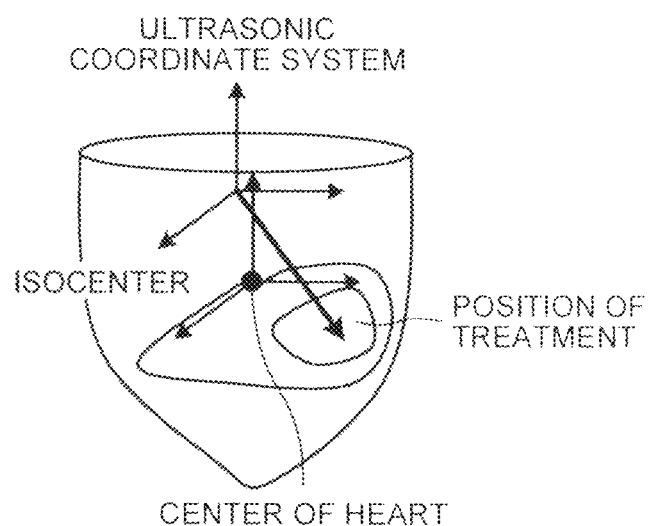

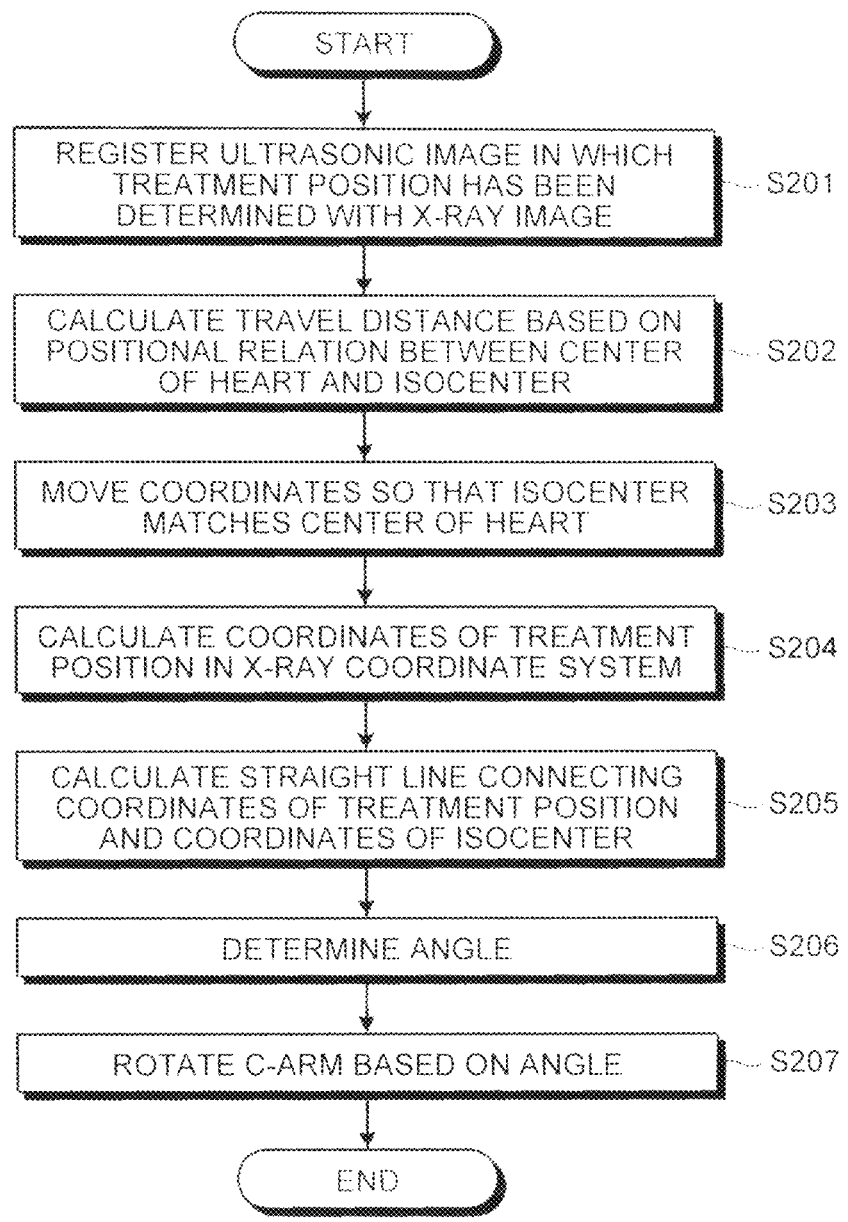

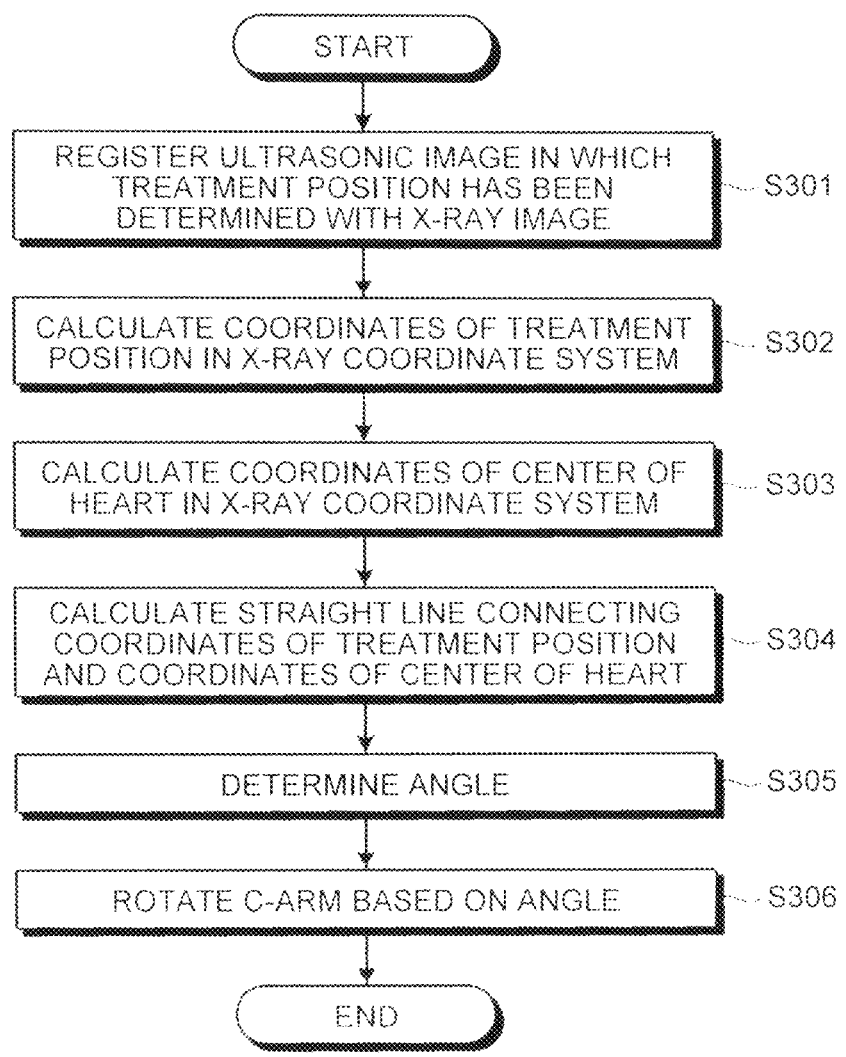

X-RAY DIAGNOSIS APPARATUS AND ARM CONTROL METHOD

CROSS-REFERENCE TO RELATED APPLICATIONS

This application is a continuation of International Application No. PCT/JP2013/075586, filed on Sep. 20, 2013 which claims the benefit of priority of the prior Japanese Patent Application No. 2012-207497, filed on Sep. 20, 2012, the entire contents of which are incorporated herein by reference.

FIELD

Embodiments described herein relate generally to an x-ray diagnosis apparatus and an arm control method.

BACKGROUND

Conventionally, the cardiac resynchronization therapy (CRT) has been known as an example of heart failure treatment. This therapy is used for treatment of a disease in which abnormality of the impulse conduction system of the heart leads to a wrong timing of motion of the cardiac muscle surrounding a ventricle, so that core-walls of the right and left ventricles do not move at the same time, and the ventricles do not contract at the correct timing, thus causing insufficient cardiac output of the blood, for example.

In the CRT, an electrode is placed in the part where the heart hardly moves (the site of latest activation) so that the ventricles of the heart contract in a synchronized manner. Specifically, in the CRT, the site of latest activation is determined through strain analysis by using an ultrasound diagnosis apparatus, and the electrode is placed on the closest vein to the site of latest activation with reference to the X-ray image radiographed by an X-ray diagnosis apparatus.

The electrode placed as described above applies stimuli electric potential at a proper timing, whereby the cardiac muscle contracts at a proper timing and controls the motion of ventricles. In the conventional technology, however, the visibility of a superimposed image of an X-ray image and an ultrasonic image may be reduced.

BRIEF DESCRIPTION OF THE DRAWINGS

FIG. 10 is a diagram for explaining an example of update processing of an angle performed by a calculating unit according to the first embodiment;

FIG. 12 is a diagram for explaining an example of processing performed by a calculating unit according to a second embodiment;

FIG. 13 is a flowchart illustrating procedures for processing performed by the X-ray diagnosis apparatus according to the second embodiment; and FIG. 14 is a flowchart illustrating procedures for processing performed by an X-ray diagnosis apparatus according to a third embodiment.

DETAILED DESCRIPTION

According to embodiment, an X-ray diagnosis apparatus comprising a calculating unit and a control unit. The calculating unit that calculates an angle between a specified position specified in an ultrasonic image generated through transmission and reception of ultrasonic waves by an ultrasound probe and a predetermined position in a radiographic space where a subject is radiographed based on information on a relative position between the radiographic space and a scanning space where the subject is scanned by the ultrasound probe. The control unit that controls an arm to move so that the subject is radiographed at the angle calculated by the calculating unit.

Figure 1:
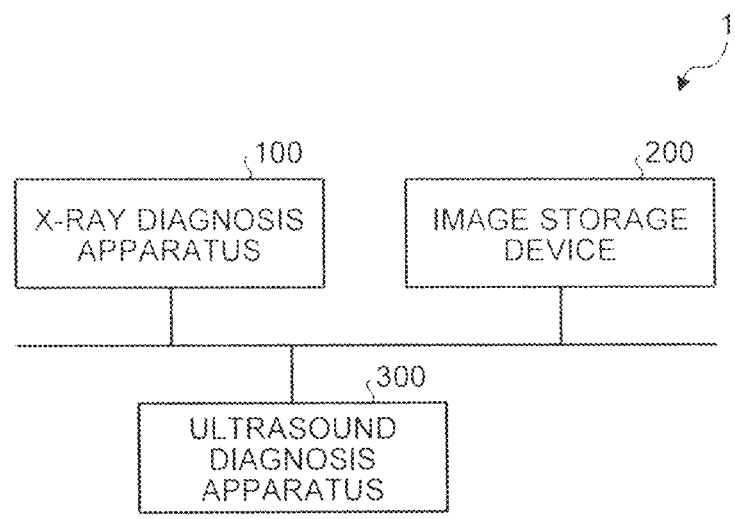
FIG. 1 is a diagram illustrating an example of the configuration of a system according to a first embodiment.

Hereinafter, embodiments of an X-ray diagnosis apparatus according to the present application are described in detail below. In a first embodiment, a system including an X-ray diagnosis apparatus according to the present application is described as an example. FIG. 1 is a diagram illustrating an example of the configuration of a system according to a first embodiment.

As illustrated in FIG. 1, a system 1 according to the first embodiment includes an X-ray diagnosis apparatus 100, an image storage device 200, and an ultrasound diagnosis apparatus 300. The apparatuses illustrated in FIG. 1 are in a communicable state directly or indirectly to each other through a local area network (LAN) provided in a hospital, for example. When a picture archiving and communication system (PACS) is implemented in the system 1, the apparatuses transmit and receive medical images to and from each other according to the digital imaging and communications in medicine (DICOM) standard.

In the system 1, the X-ray diagnosis apparatus 100 acquires X-ray images according to the operations of the engineer (operator) of the apparatus and the ultrasound diagnosis apparatus 300 acquires ultrasonic images according to the operations of the engineer (operator) of the apparatus. The X-ray diagnosis apparatus 100 then displays the ultrasonic image appropriately registered with the X-ray image. This enables a doctor to place an electrode on a placing position planned using the ultrasound diagnosis apparatus in a precise manner while performing the cardiac resynchronization therapy (CRT).

The image storage device 200 is a database that stores medical images. Specifically, the image storage device 200 according to the first embodiment records ultrasonic images transmitted from the ultrasound diagnosis apparatus 300 in a storage unit and stores the images therein. That is, the X-ray diagnosis apparatus 100 according to the first embodiment may receive the image data directly from the ultrasound diagnosis apparatus 300, and may acquire the images temporarily stored in the image storage device 200.

Figure 2:
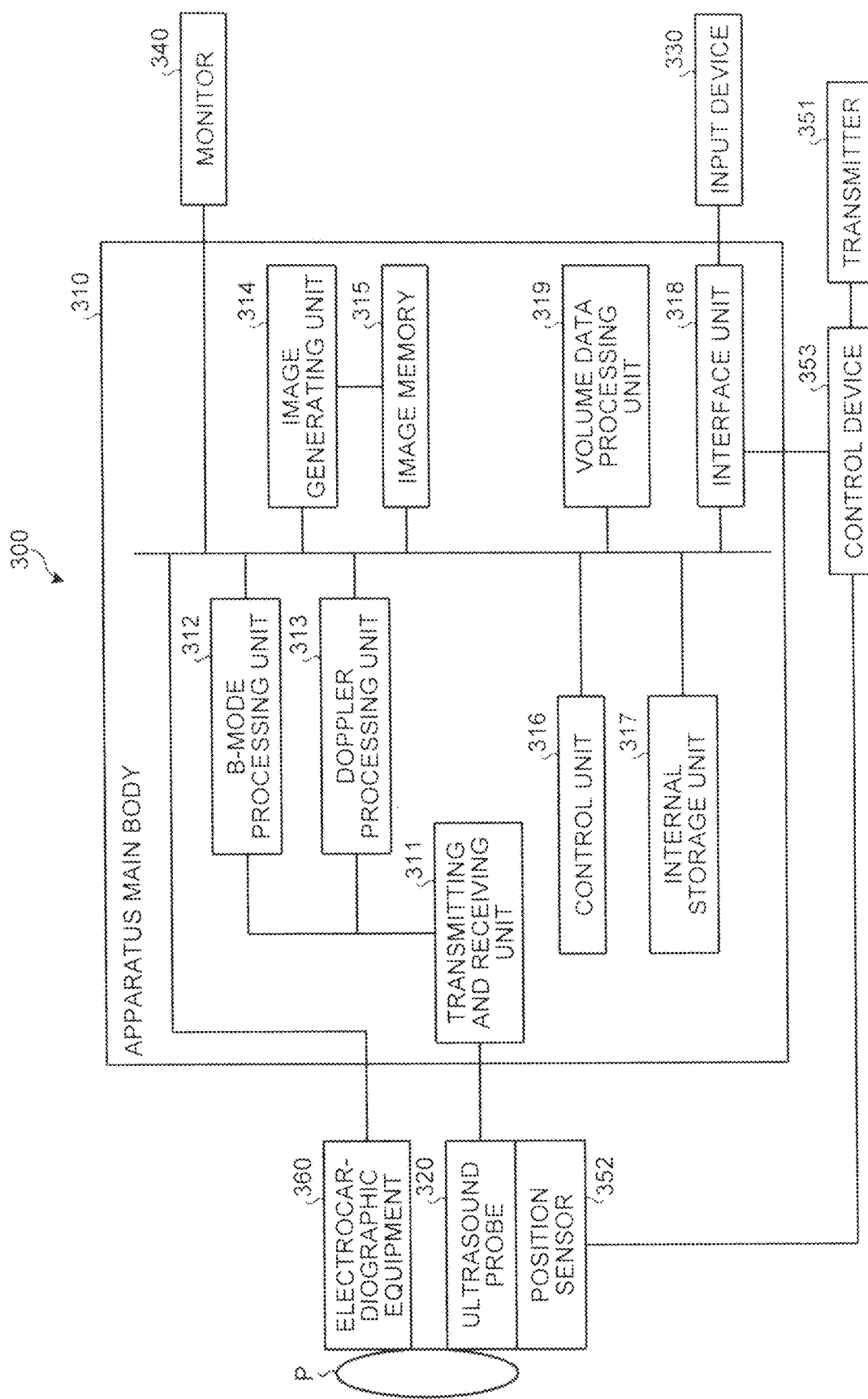
FIG. 2 is a diagram for explaining the configuration of an ultrasound diagnosis apparatus according to the first embodiment.

The following describes the configuration of the ultrasound diagnosis apparatus according to the first embodiment with reference to FIG. 2. FIG. 2 is a diagram for explaining the configuration of the ultrasound diagnosis apparatus 300 according to the first embodiment. As illustrated in FIG. 2, the ultrasound diagnosis apparatus 300 according to the first embodiment includes an apparatus main body 310, an ultrasound probe 320, an input device 330, a monitor 340, a transmitter 351, a position sensor 352, a control device 353, and electrocardiographic equipment 360.

The ultrasound probe 320 includes a plurality of piezoelectric transducer elements that generate ultrasound based on driving signals supplied from a transmitting and receiving unit 311 included in the apparatus main body 310, which will be described later. In addition, the ultrasound probe 320 receives a reflected wave from the subject P and converts it into electrical signals. The ultrasound probe 320 includes a matching layer provided for the piezoelectric transducer elements, and a backing material that prevents the ultrasound of piezoelectric transducer elements from being transmitted backward. For example, the ultrasound probe 320 is a sector ultrasound probe, a linear ultrasound probe, or a convex ultrasound probe.

When the ultrasonic wave is transmitted from the ultrasound probe 320 to the subject P, the transmitted ultrasonic wave is sequentially reflected on discontinuity surfaces of acoustic impedance in internal body tissues of the subject P, and received by a plurality of piezoelectric transducer elements included in the ultrasound probe 320 as reflected wave signals. The amplitude of the received reflected wave signals depends on the difference of the acoustic impedance on the surfaces of discontinuity where the ultrasonic wave is reflected. It should be noted that the reflected wave signals obtained when the transmitted ultrasound pulse is reflected on the surfaces of a moving bloodstream or a moving cardiac wall (i.e., moving object) receives frequency shift depending on the velocity component with respect to the ultrasound transmission direction of the moving object due to the Doppler effect.

In the present embodiment, the subject P is scanned in three dimensions by the ultrasound probe 320. The ultrasound probe 320 may mechanically swing and move a plurality of piezoelectric transducer elements of a one-dimensional ultrasound probe. The ultrasound probe 320 may be a two-dimensional ultrasound probe having a plurality of piezoelectric transducer elements arranged in two dimensions in a matrix shape.

The input device 330 includes a trackball, a switch, a button, and a touch command screen and receives various types of setting demands from an operator of the ultrasound diagnosis apparatus 300. The input device 330 then transfers the received various types of setting demands forward to the apparatus main body 310. For example, the input device 330 receives various types of operations relating to registration of an ultrasonic image and an X-ray image.

The monitor 340 displays a graphical user interface (GUI) used for inputting various types of setting demands by the operator of the ultrasound diagnosis apparatus 300 using the input device 330. The monitor 340 also displays side by side an ultrasonic image and an X-ray computed tomography (CT) image generated in the apparatus main body 310.

The transmitter 351 transmits a reference signal. Specifically, the transmitter 351 is disposed in an arbitrary position and forms a magnetic field outward with itself as the center of the magnetic field. The position sensor 352 receives the reference signal, thereby acquiring the positional information in the three-dimensional space. Specifically, the position sensor 352 is mounted on the surface of the ultrasound probe 320 and detects the three-dimensional magnetic field formed by the transmitter 351. The position sensor 352 then converts information of the detected magnetic field into signals and outputs the signals to the control device 353.

The control device 353 calculates the coordinates and the orientation of the position sensor 352 in the space having the transmitter 351 as its origin based on the signals received from the position sensor 352. The control device 353 then outputs the calculated coordinates and orientation to a control unit 316 of the apparatus main body 310. It should be noted that the diagnosis of the subject P is performed in the magnetic field area where the position sensor 352 mounted on the ultrasound probe 320 can precisely detect the magnetic field of the transmitter 351. In the embodiment, a magnetic sensor is used as a sensor that acquires positional information, however, the embodiment is not limited to this example. An infrared sensor, an optical sensor, or a camera may be used instead of the magnetic sensor.

The electrocardiographic equipment 360 is coupled to the apparatus main body 310 and acquires an electrocardiogram (ECG) of the subject P on which ultrasound scanning is performed. The electrocardiographic equipment 360 transmits the acquired electrocardiogram and time information to the apparatus main body 310.

Figure 3:
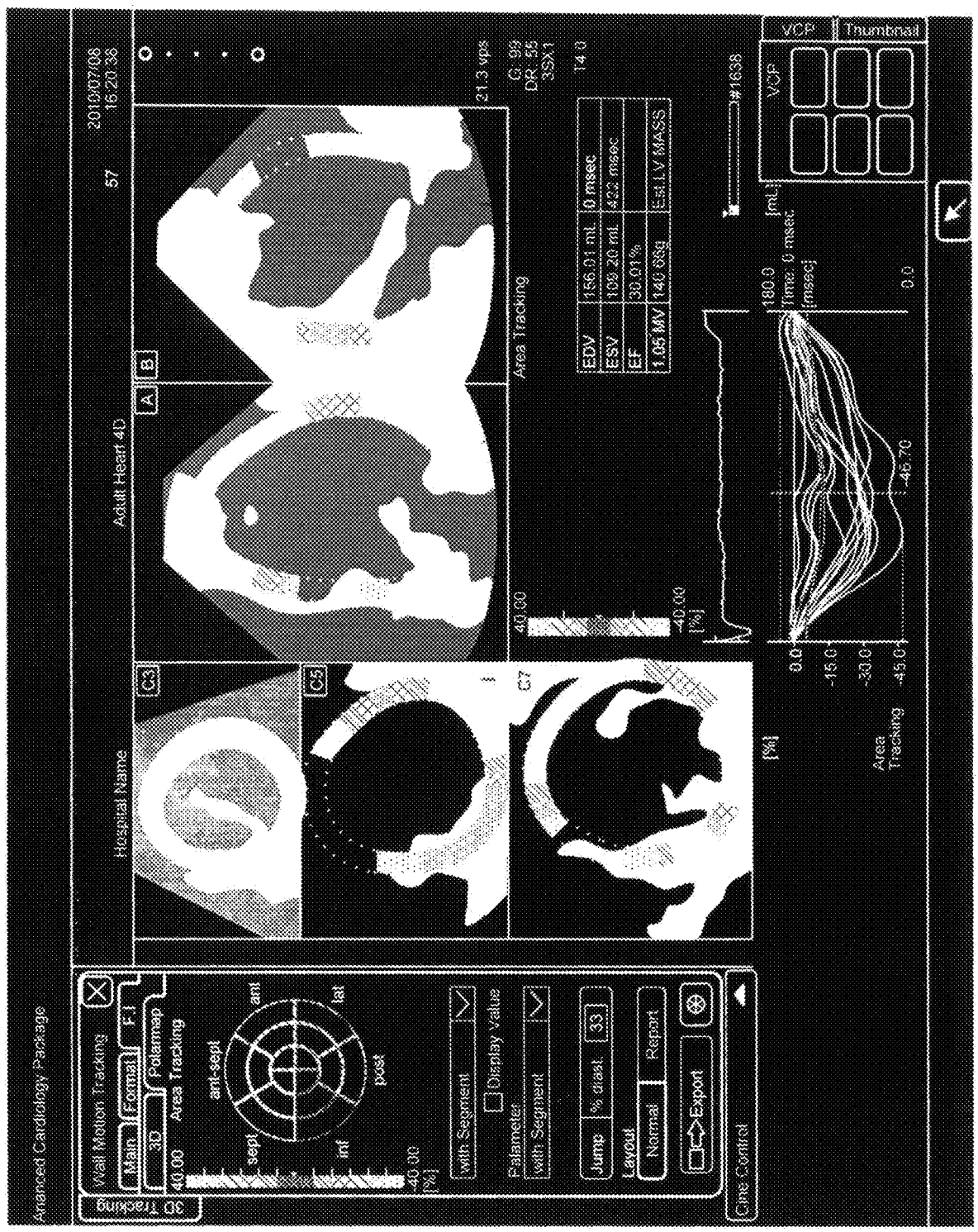
FIG. 3 is a diagram illustrating an example of processing results obtained by a volume data processing unit according to the first embodiment.

The apparatus main body 310 is an apparatus that generates ultrasonic images based on the reflected wave received by the ultrasound probe 320. As illustrated in FIG. 3, the apparatus main body 310 includes a transmitting and receiving unit 311, a B-mode processing unit 312, a Doppler processing unit 313, an image generating unit 314, an image memory 315, a control unit 316, an internal storage unit 317, an interface unit 318, and a volume data processing unit 319.

The transmitting and receiving unit 311 includes a trigger generating circuit, a delay circuit, and a pulser circuit, and supplies driving signals to the ultrasound probe 320. The pulser circuit repeatedly generates rate pulses for forming ultrasonic waves to be transmitted at a predetermined rate frequency. The delay circuit supplies a delay time necessary to converge the ultrasonic waves generated from the ultrasound probe 320 into a beam for each of the piezoelectric transducer elements and to determine the transmission directionality, to each of rate pulses generated by the pulser circuit. The trigger generating circuit applies driving pulses to the ultrasound probe 320 at a timing based on the rate pulses. That is, the delay circuit changes the delay time supplied to each of the rate pulses, thereby arbitrarily adjusting the transmission direction from the surface of the piezoelectric transducer elements.

The transmitting and receiving unit 311 includes an amplifier circuit, an A/D converter, and an adder. The transmitting and receiving unit 311 performs various types of processing on the reflected wave signals received by the ultrasound probe 320 and generates reflected wave data. The amplifier circuit amplifies the reflected wave signals for each channel and performs gain correction processing. The A/D converter supplies a delay time necessary to perform A/D-conversion on the reflected wave signals on which gain correction has been performed and to determine transmission directionality. The adder performs addition processing on the reflected wave signals processed by the A/D converter, thereby generating the reflected wave data. The addition processing performed by the adder enhances a reflect component from the direction corresponding to the reception directionality of the reflected wave signals.

As described above, the transmitting and receiving unit 311 controls the transmission directivity and the reception directionality in transmitting and receiving ultrasound. The transmitting and receiving unit 311 has a function capable of instantly change delay information, a transmission frequency, a transmission drive voltage, the number of aperture elements under the control of the control unit 316, which will be described later. In particular, changes in the transmission drive voltage can be achieved with, a linear amplifier oscillation circuit capable of instantly changing a value, or a mechanism for electrically changing a plurality of power units. The transmitting and receiving unit 311 is capable of transmitting and receiving different waveforms for each frame or each rate.

The B-mode processing unit 312 receives from the transmitting and receiving unit 311, the reflected wave data that is the processed reflected wave signals on which gain correction processing, A/D conversion processing, and addition processing have been performed. The B-mode processing unit 312 then performs logarithm amplification and envelope detection processing, for example, on the received data, thereby generating data in which the signal intensity is represented with the level of brightness (B-mode data).

The Doppler processing unit 313 performs frequency analysis of the speed information using the reflected wave data received from the transmitting and receiving unit 311. The Doppler processing unit 313 then extracts a bloodstream echo component, a tissue echo component, and a contrast material echo component due to the Doppler effect and generates data in which the moving object information such as the average speed, distribution, and power is extracted at multiple points (Doppler data).

The image generating unit 314 generates ultrasonic images from the B-mode data generated by the B-mode processing unit 312 and the Doppler data generated by the Doppler processing unit 313. Specifically, the image generating unit 314 converts scanning line signal arrays of the ultrasound scanning into scanning line signal arrays in a video format typically used in televisions (scan conversion), thereby generating ultrasonic images (e.g., B-mode images and Doppler images) from the B-mode data and the Doppler data. The image generating unit 314 associates the generated ultrasonic images with the electrocardiogram and the time information received from the electrocardiographic equipment 360 and stores them in the image memory 315.

The image memory 315 stores therein image data such as an enhanced image and a tissue image generated by the image generating unit 314. The image memory 315 also stores therein output signals just passed through the transmitting and receiving unit 311, i.e., radio frequency (RF), the brightness signals of the images, various types of raw data, and image data acquired through a network as necessary. The data format of the image data stored in the image memory 315 may be a data format after being converted into a video format to be displayed on the monitor 340 by the control unit 316, which will be described below, or a data format before being converted into coordinates, which is raw data generated by the B-mode processing unit 312 and the Doppler processing unit 313.

The control unit 316 controls the overall processing performed on the ultrasound diagnosis apparatus 300. Specifically, the control unit 316 controls various types of processing performed by the transmitting and receiving unit 311, the B-mode processing unit 312, the Doppler processing unit 313, and the image generating unit 314 based on various types of setting demands input by an operator through the input device 330, various types of control programs and various types of setting information retrieved from the internal storage unit 317. The control unit 316 also controls the monitor 340 to display thereon the ultrasonic images stored in the image memory 315. The control unit 316 transmits and receives three-dimensional image data (volume data) acquired by other modalities (e.g., an X-ray CT apparatus, an MRI apparatus) through a network according to the digital imaging and communications in medicine (DICOM) standard, for example.

The internal storage unit 317 stores therein control programs for transmitting and receiving the ultrasonic wave, and for image processing and display processing, and various types of data such as diagnosis information (e.g., patient IDs, observations by a doctor) and a diagnosis protocol. The internal storage unit 317 is also used for storing the images stored in the image memory 315 as necessary.

The interface unit 318 is an interface that controls exchanging various types of information between the input device 330, a control device 353, and the apparatus main body 310. The interface unit 318 controls transfer of the positional information acquired by the control device 353 to the control unit 316.

The volume data processing unit 319 executes various types of processing relating to strain analysis. Specifically, through a 3D wall motion tracking technology, an image is generated in which excitation propagation in the heart is drawn. The ultrasound diagnosis apparatus 300 according to the first embodiment here firstly generates the volume data of the heart of the subject P. For example, the ultrasound diagnosis apparatus 300 according to the first embodiment generates a plurality of pieces of volume data (a volume data group) by radiographing the left ventricle (LV) of the heart of the subject P along time series during a period of one or more heartbeats.

The volume data processing unit 319 generates motion information on the motion of the core wall, from each piece of the volume data group along time series generated by scanning the heart of the subject P three-dimensionally with the ultrasound. Specifically, the volume data processing unit 319 generates motion information by pattern matching between the pieces of the volume data. More specifically, the volume data processing unit 319 tracks the tracking points that have been set in a cardiac muscle tissue drawn in each piece of the volume data based on speckle patterns, thereby calculating motion vectors of the respective tracking points. The volume data processing unit 319 then uses the motion vectors of the respective tracking points, thereby generating motion information that represents the motion of a local cardiac muscle. In other words, the volume data processing unit 319 performs three-dimensional speckle tracking and generates motion information. For example, the volume data processing unit 319 generates the local area change rate in the cardiac tissue as motion information.

FIG. 3 is a diagram illustrating an example of processing results obtained by the volume data processing unit 319 according to the first embodiment. For example, the volume data processing unit 319 can generate a superimposed image in which a specific area is superimposed onto a polar map image through a "time phase holding display method" as illustrated on the left side of FIG. 3. In FIG. 3, "ant-sept" refers to "anteroseptal", "ant" refers to an anterior wall, "lat" refers to a lateral wall, "post" refers to a posterior wall, "inf" refers to an inferior wall, and "sept" refers to "septum".

The volume data processing unit 319 can compose an image from an electrocardiogram and a graph of time change curves of the average motion information (average changing rate of area) for 16 fractions in addition to the time phase holding superimposed image, as illustrated on the bottom in FIG. 3. In FIG. 3, time change curves of the average changing rate of area for each of the 16 fractions are represented with solid lines. Actually, however, the volume data processing unit 319 colors the respective time change curves of the average motion information for each of the 16 fractions in respective colors allocated to each fraction so that it can be understood which time change curve of the average motion information corresponds to which fractions.

The volume data processing unit 319 also generates a plurality of MPR images with a cross section having a short axis or with a cross section having a longitudinal axis from the volume data. In the example illustrated in FIG. 3, the volume data processing unit 319 generates a composite image in the area A. In composite image, a superimposed image including images of a specific area superimposed through the time phase holding method is disposed on the left ventricular core-wall in an apical four-chamber image. In addition, in the example illustrated in FIG. 3, the volume data processing unit 319 generates a composite image in the area B. In composite image, a superimposed image including images of a specific area superimposed through the time phase holding method is disposed on the left ventricular core-wall in an apical two-chamber image.

Furthermore, in the example illustrated in FIG. 3, the volume data processing unit 319 generates a composite image in the area C3. In composite image, a superimposed image including images of a specific area superimposed through the time phase holding method is disposed on the left ventricular core-wall in the image with a cross section having a short axis in the vicinity of the apex. Still furthermore, in the example illustrated in FIG. 3, the volume data processing unit 319 generates a composite image in the area C5. In composite image, a superimposed image including images of a specific area superimposed through the time phase holding method is disposed on the left ventricular core-wall of an image with a cross section having a short axis located between the apex and the base. Still furthermore, in the example illustrated in FIG. 3, the volume data processing unit 319 generates a composite image in the area C7. In the composite image, a superimposed image including images of a specific area superimposed through the time phase holding method is disposed on the left ventricular core-wall in the image with a cross section having a short axis in the vicinity of the base.

In the example illustrated in FIG. 3, together with a color bar and the electrocardiogram, values of various types of motion information are provided as a table. The EDV illustrated in FIG. 3 refers to the volume of the cardiac lumen in the time phase of an end diastole (ED). In the example illustrated in FIG. 3, the EDV indicates "156.01 mL" and the time of the end diastole (reference time phase) indicates "0 msec". The ESV illustrated in FIG. 3 refers to the volume of the cardiac lumen in the time phase of an end systole (ES). In the example illustrated in FIG. 3, the ESV indicates "109.20 mL" and the time of the end systole indicates "422 msec".

The EF illustrated in FIG. 3 refers to the ejection fraction determined from the EDV and the ESV. In the example illustrated in FIG. 3, the EF indicates "30.01%". "1.05×MV" illustrated in FIG. 3 refers to the "cardiac mass (g)" obtained by multiplying the cardiac muscle volume (MV) by the average value of the density of cardiac muscle "1.05 g/mL". In the example illustrated in FIG. 3, "1.05×MV" indicates "140.66 g". Furthermore, in the example illustrated in FIG. 3, "est. LV MASS" is represented; which indicates that the value "140.66 g" is estimated from the cardiac muscle volume of the left ventricle.

Figure 4A:
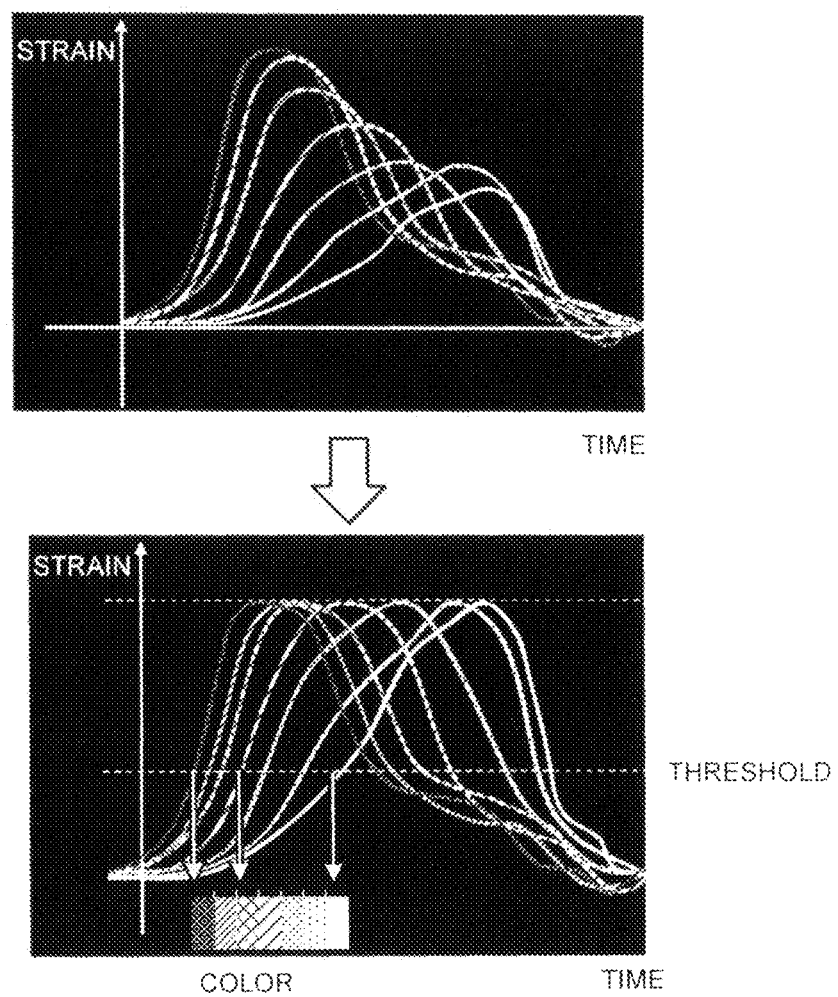
FIG. 4A is a diagram illustrating an example of processing performed by the volume data processing unit according to the first embodiment.

The volume data processing unit 319 may calculate the time change rate (referred to as an "area change rate") of the change in a local area (referred to as a "local area change") as the motion information. That is, the volume data processing unit 319 may calculate the area change rate of the changing rate of area by estimating the time differential value of the local area change. On this occasion, the volume data processing unit 319 changes the color tones of the superimposed image as illustrated in FIG. 4A, by allocating a color for each predetermined threshold time. FIG. 4A is a diagram for explaining an example of processing performed by the volume data processing unit 319 according to the first embodiment.

Figure 4B:
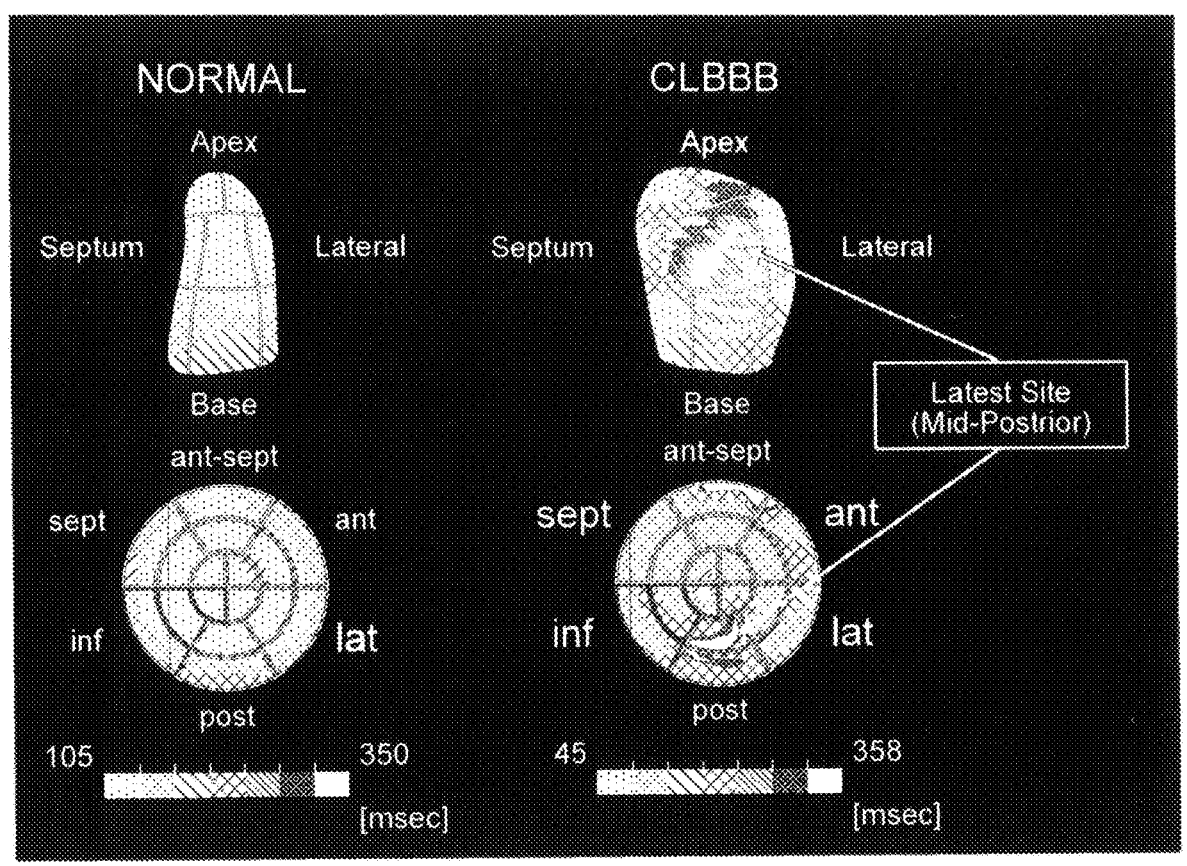
FIG. 4B is a diagram illustrating an example of images generated by the volume data processing unit according to the first embodiment.

FIG. 4B is a diagram illustrating an example of images generated by the volume data processing unit 319 according to the first embodiment. FIG. 4B illustrates the images in which some aspects of excitation propagation in the heart are drawn. Specifically, two following types of superimposed images are illustrated for both an aspect of normal (NORMAL) and an aspect of complete left bundle branch block (CLBBB) in FIG. 4B: the superimposed image color tones are superimposed onto the surface rendering images; and the superimposed image color tones are superimposed onto the polar map images. In the images for CLBBB, sites of latest activation are represented.

Figure 5:
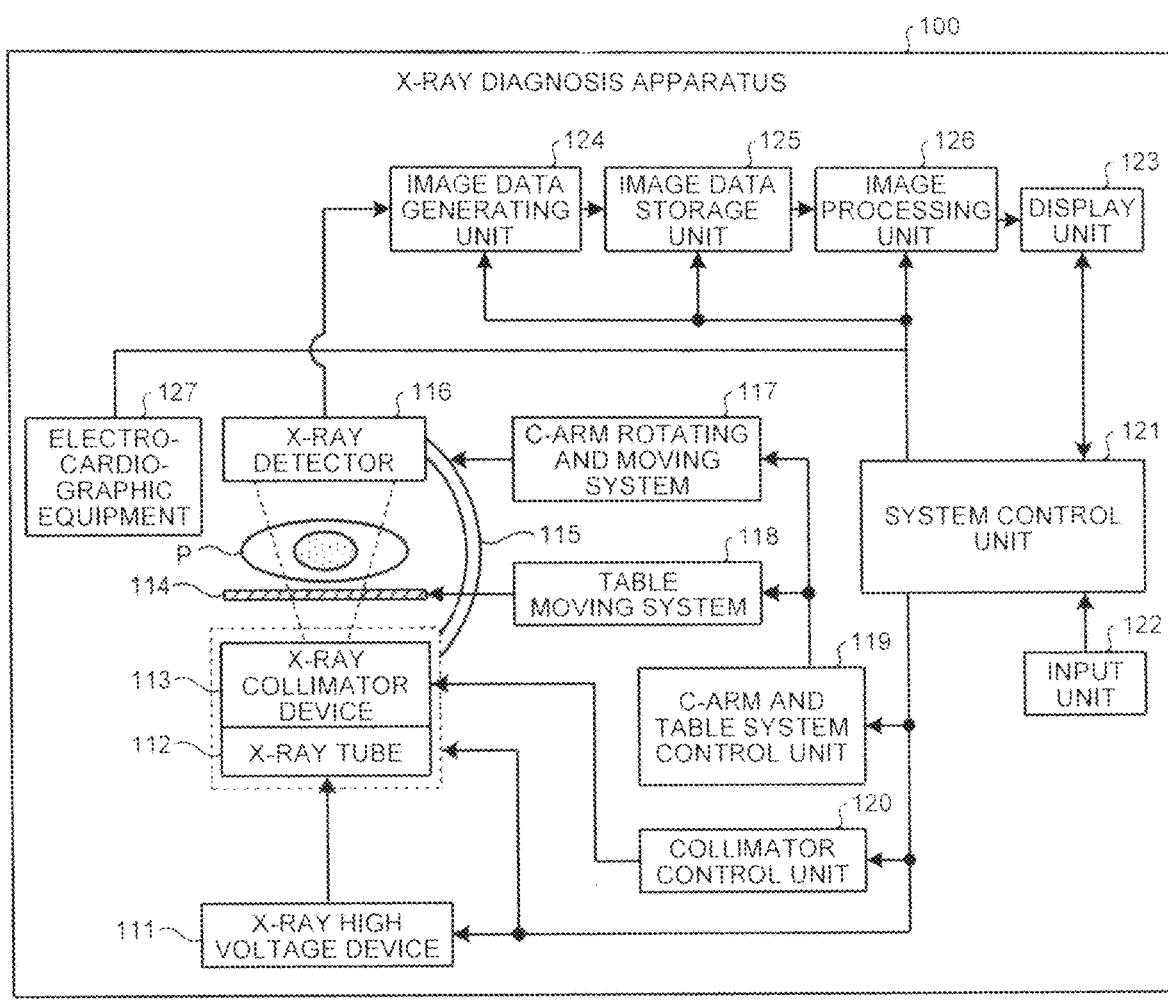
FIG. 5 is a diagram illustrating an example of the configuration of an X-ray diagnosis apparatus according to the first embodiment.

The following describes the configuration of the X-ray diagnosis apparatus 100 according to the first embodiment. FIG. 5 is a diagram illustrating an example of the configuration of the X-ray diagnosis apparatus 100 according to the first embodiment. As illustrated in FIG. 5, the X-ray diagnosis apparatus 100 according to the first embodiment includes an X-ray high voltage device 111, an X-ray tube 112, an X-ray collimator device 113, a table 114, a C-arm 115, and an X-ray detector 116. The X-ray diagnosis apparatus 100 according to the first embodiment also includes a C-arm rotating and moving system 117, a table moving system 118, a C-arm and table system control unit 119, a collimator control unit 120, a system control unit 121, an input unit 122, and a display unit 123. Furthermore, the X-ray diagnosis apparatus 100 according to the first embodiment includes an image data generating unit 124, an image data storage unit 125, an image processing unit 126, and electrocardiographic equipment 127.

The X-ray high voltage device 111 generates a high voltage under the control of the system control unit 121 and supplies the generated high voltage to the X-ray tube 112. The X-ray tube 112 generates X-rays using the high voltage supplied from the X-ray high voltage device 111.

The X-ray collimator device 113 narrows down the X-rays generated by the X-ray tube 112 under the control of the collimator control unit 120 so that the region of interest of a subject P is selectively irradiated with the X-rays. For example, the X-ray collimator device 113 includes four slidable collimator blades. The X-ray collimator device 113 slides the collimator blades under the control of the collimator control unit 120, thereby narrowing down the X-rays generated by the X-ray tube 112 so that the subject P is irradiated with the X-rays. The table 114 is a bed for mounting the subject P and is disposed on a not-illustrated couch. The subject P is not included in the X-ray diagnosis apparatus 100.

The X-ray detector 116 detects the X-rays transmitted through the subject P. For example, the X-ray detector 116 includes detecting elements arranged in a matrix shape. Each of the detecting elements converts the X-ray transmitted through the subject P into the electrical signals, accumulates them, and transmits the accumulated electrical signals to the image data generating unit 124.

The C-arm 115 retains the X-ray tube 112, the X-ray collimator device 113, and the X-ray detector 116. The X-ray tube 112 and the X-ray collimator device 113 are disposed on an opposite side of the X-ray detector 116 across the subject P and supported by the C-arm 115.

The C-arm rotating and moving system 117 is a system for rotating and moving the C-arm 115. The table moving system 118 is a system for moving the table 114. The C-arm and table system control unit 119 controls the C-arm rotating and moving system 117 and the table moving system 118 under the control of the system control unit 121, thereby adjusting the rotation and movement of the C-arm 115, and the movement of the table 114. The collimator control unit 120 adjusts the degree of opening of the collimator blades included in the X-ray collimator device 113 under the control of the system control unit 121, thereby controlling the radiation range of the X-rays with which the subject P is irradiated.

The electrocardiographic equipment 127 acquires an electrocardiogram (ECG) of the subject P to which not-illustrated terminals are attached. The electrocardiographic equipment 127 then transmits the acquired electrocardiogram together with time information to the image data generating unit 124 and the image processing unit 126.

The image data generating unit 124 generates an X-ray image using the electrical signals converted by the X-ray detector 116 from the X-rays, and stores the generated X-ray image in the image data storage unit 125. For example, the image data generating unit 124 performs various types of processing such as current-voltage conversion, analog-digital (A/D) conversion, and parallel-serial conversion on the electrical signals received from the X-ray detector 116, thereby generating an X-ray image.

More specifically, the image data generating unit 124 radiographs along time series the heart of the subject P into which a contrast material has been injected, thereby generating a plurality of X-ray images. The image data generating unit 124 stores the generated X-ray images in the image data storage unit 125. Specifically, the image data generating unit 124 according to the present embodiment associates the generated X-ray images with the electrocardiogram and the time information received from the electrocardiographic equipment 127 and stores them in the image data storage unit 125.

The image data storage unit 125 stores therein the X-ray images generated by the image data generating unit 124. For example, the image data storage unit 125 associates the X-ray images generated by the image data generating unit 124 with the radiography time and the electrocardiogram during the radiography time and stores them. The image processing unit 126 performs various types of image processing on the image data stored in the image data storage unit 125. For example, the image processing unit 126 processes a plurality of X-ray images obtained through radiography along time series and stored in the image data storage unit 125, thereby generating a moving image.

The input unit 122 receives various types of instructions from an operator such as a doctor and an engineer who operates the X-ray diagnosis apparatus 100. For example, the input unit 122 includes a mouse, a keyboard, a button, a trackball, and a joystick, for example. The input unit 122 transfers the instruction received from the operator forward to the system control unit 121. For example, the input unit 122 receives an instruction for turning ON the power of the X-ray diagnosis apparatus 100.

The display unit 123 displays a graphical user interface (GUI) for receiving instructions by the operator, and image data stored in the image data storage unit 125. For example, the display unit 123 includes a monitor. The display unit 123 may include a plurality of monitors.

The system control unit 121 controls the overall operations of the X-ray diagnosis apparatus 100. For example, the system control unit 121 controls the X-ray high voltage device 111 according to the operator's instruction forwarded from the input unit 122 to adjust the voltage supplied to the X-ray tube 112, thereby controlling the amount of X-rays or turning ON and OFF for emitting X-rays with which the subject P is irradiated. For another example, the system control unit 121 controls the C-arm and table system control unit 119 according to the operator's instruction to adjust the rotation and movement of the C-arm 115, and the movement of the table 114. For still another example, the system control unit 121 controls the collimator control unit 120 according to the operator's instruction to adjust the degree of opening of the collimator blades included in the X-ray collimator device 113, thereby controlling the radiation range of the X-ray with which the subject P is irradiated.

The system control unit 121 controls image data generating processing performed by the image data generating unit 124, image processing performed by the image processing unit 126, or analysis processing according to the operator's instruction by the operator. The system control unit 121 performs control for displaying on the monitor or monitors of the display unit 123 a graphical user interface (GUI) for receiving instructions by the operator and images stored in the image data storage unit 125.

In the X-ray diagnosis apparatus 100 according to the first embodiment, the CRT is performed. In the CRT, the site of latest activation is determined from the superimposed image as illustrated in FIG. 4B, and an electrode (a pacing lead) is placed on the closest vein to the site of latest activation with reference to an X-ray image obtained by using a contrast material. On this occasion, however, the position of the site of latest activation is not accurately represented in the X-ray image. A doctor may therefore perform manipulation trusting his/her own intuition, resulting in placing the electrode in a wrong position. To avoid this, an ultrasound superimposed image is further superimposed onto the site of latest activation in the X-ray image, thereby helping a doctor to place the electrode in the correct position. On this occasion, depending on the orientation of superimposing the X-ray image and the ultrasonic image, the site of latest activation cannot be observed from an anterior view, whereby the visibility of a superimposed image of the X-ray image and the ultrasonic image may be reduced.

In the X-ray diagnosis apparatus 100 according to the first embodiment, the control by the system control unit 121, which will be described in detail, is used for achieving suppression of the reduction of the visibility of a superimposed image of the X-ray image and the ultrasonic image. The superimposed image of the X-ray image and the ultrasonic image is referred to as a fused image.

Figure 6:
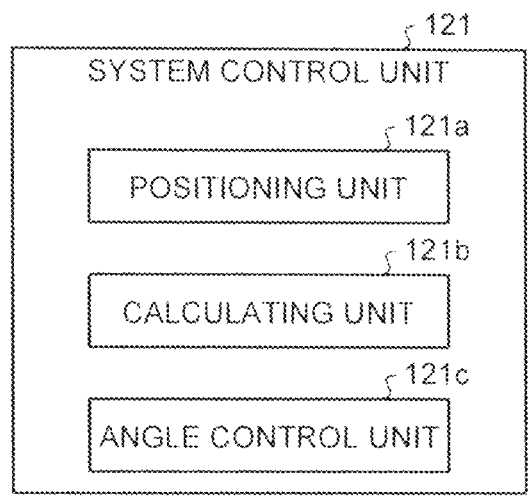
FIG. 6 is a diagram illustrating an example of the configuration of a system control unit according to the first embodiment.

FIG. 6 is a diagram illustrating an example of the configuration of the system control unit 121 according to the first embodiment. As illustrated in FIG. 6, the system control unit 121 includes a positioning unit 121a, a calculating unit 121b, and an angle control unit 121c. The system control unit 121 controls the angle of the arm when radiographing, so that the site of latest activation in a fused image can be observed from an anterior view.

Figure 7:
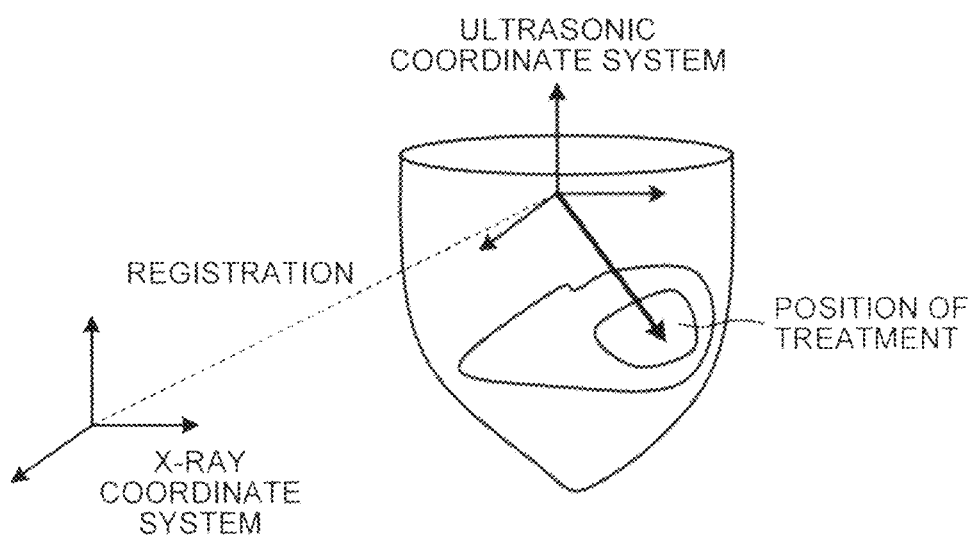
FIG. 7 is a diagram for explaining an example of processing performed by a positioning unit according to the first embodiment.

The positioning unit 121a performs the registration for superimposing an X-ray image and an ultrasonic image. Specifically, the positioning unit 121a associates an X-ray coordinate system with an ultrasound coordinate system from the relative positional relation therebetween. The X-ray coordinate system represents an X-ray image with the coordinates in a space where the X-ray image is radiographed, whereas the ultrasonic coordinate system represents an ultrasonic image with the coordinates in a space where the ultrasonic image is captured. FIG. 7 is a diagram for explaining an example of processing performed by a positioning unit 121a according to the first embodiment.

For example, as illustrated in FIG. 7, the positioning unit 121a determines the position of the ultrasound coordinate system in the X-ray coordinate system. That is, the positioning unit 121a determines where in the X-ray coordinate system the coordinate space in which the ultrasonic images are acquired corresponds to. This enables the positioning unit 121a to clarify where in the X-ray coordinate system the treatment position locates and which angle provides the front view of the treatment position in the image. Examples of registration methods performed by the positioning unit 121a here include the following three methods.

A first method adopts a position sensor. For example, the ultrasound probe 320 having the position sensor 352 is radiographed by the X-ray diagnosis apparatus 100. The positioning unit 121a then calculates the coordinates of the ultrasound probe 320 in the X-ray coordinate system from the position of the ultrasound probe 320 included in the radiographed X-ray image. Subsequently, the positioning unit 121a acquires the positional information of the position sensor 352 when the X-ray image is radiographed from the ultrasound diagnosis apparatus 300. That is, the positioning unit 121a acquires the coordinates of the ultrasound probe 320 in the ultrasound coordinate system when the X-ray image is radiographed.

The positioning unit 121a associates the coordinates of the ultrasound probe 320 in the X-ray coordinate system with the coordinates of the ultrasound probe 320 in the ultrasound coordinate system when the X-ray image is radiographed, thereby determining the position of the ultrasound coordinate system in the X-ray coordinate system. This enables the positioning unit 121a to calculate the coordinates of the determined position of the treatment location using the ultrasonic image in the X-ray coordinate system.

A second method adopts a landmark. For example, an observer sets a landmark in an ultrasonic image for a certain part that can be checked in an X-ray image. The positioning unit 121a registers the ultrasonic image with the X-ray image using the landmark set in the ultrasonic image and the position corresponding to the landmark in the X-ray image. For example, a wall of a ventricle in the ultrasonic image is set as a landmark. The positioning unit 121a registers the X-ray coordinate system with the ultrasound coordinate system using the enhanced X-ray image and the ultrasonic image in which the landmark is set.

A third method adopts a computed tomography (CT) image. For example, the positioning unit 121a registers an ultrasonic image with a CT image, thereby locating the ultrasound coordinate system in the CT coordinate system. The positioning unit 121a registers the X-ray image with the CT image, thereby locating the X-ray coordinate system in the CT coordinate system. The positioning unit 121a then locates the ultrasound coordinate system in the X-ray coordinate system using the position of the ultrasound coordinate system in the CT coordinate system, and the position of the X-ray coordinate system in the CT coordinate system.

As described above, the positioning unit 121a locates the ultrasound coordinate system in the X-ray coordinate system, thereby correctly calculating where the position of the treatment determined in the ultrasonic image is located in the X-ray image. It should be noted that the registration methods as described above are only examples, and the embodiment is not limited thereto. That is, any other method can be used as long as the ultrasound coordinate system can be located in the X-ray coordinate system.

With reference to FIG. 6 again, the calculating unit 121b calculates the angle between a specified position specified in the ultrasonic image generated through transmission and reception of ultrasonic waves by the ultrasound probe and a predetermined position in the radiographic space based on the information on the relative position between the radiographic space where a subject is radiographed and the scanning space where the subject is scanned by the ultrasound probe. Specifically, the calculating unit 121b calculates the coordinates of the site of latest activation (the treatment position) in the X-ray coordinate system from the X-ray image and the ultrasonic image registered with each other by the positioning unit 121a. The calculating unit 121b then calculates the straight line connecting the calculated coordinates of the treatment position and a predetermined position, thereby calculating the angle of the calculated straight line.

Figure 8:
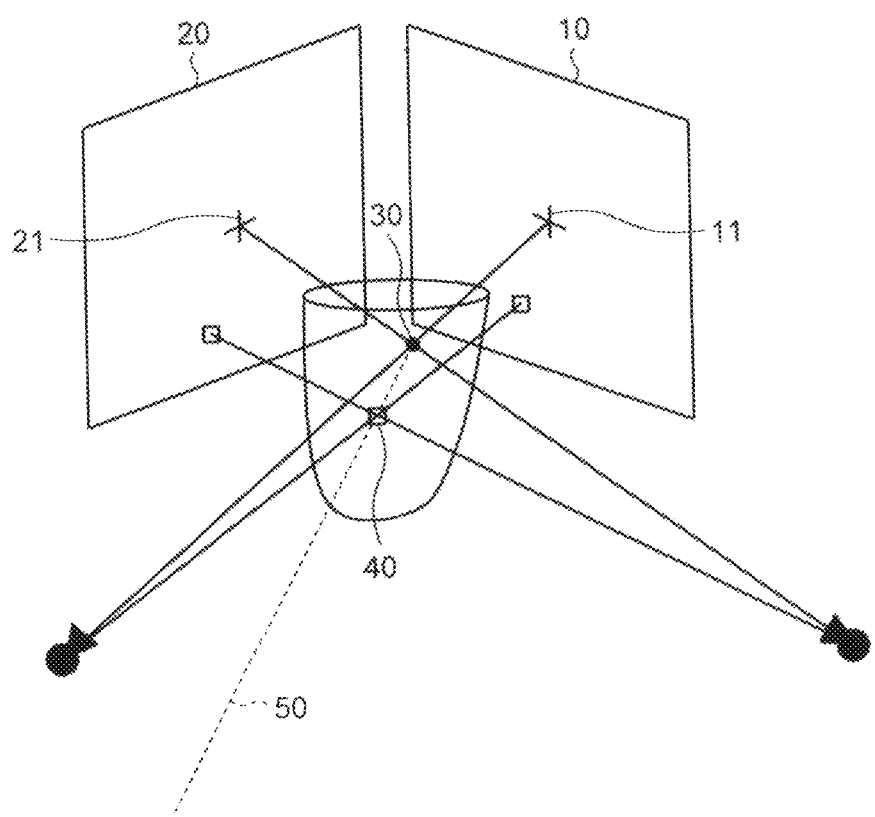
FIG. 8 is a diagram for explaining an example of processing performed by a calculating unit according to the first embodiment.

The calculating unit 121b determines the isocenter as a predetermined position and the center of the radiographic space as the isocenter. For example, the calculating unit 121b calculates the intersection point of the centers of images in X-ray images obtained through radiography in the radiographic space and determines the calculated intersection point as the isocenter. FIG. 8 is a diagram for explaining an example of processing performed by a calculating unit 121b according to the first embodiment. FIG. 8 illustrates the processing after two images, the X-ray image and the ultrasonic image are registered with each other by the positioning unit 121a.

For example, as illustrated in FIG. 8, the calculating unit 121b calculates the straight line from the X-ray source of an X-ray image 10 to a center of image 11 and the straight line from the X-ray source of an X-ray image 20 to a center of image 21. The calculating unit 121b then determines the intersection point of the calculated two straight lines as an isocenter 30. The calculating unit 121b subsequently calculates a straight line 50 connecting the coordinates in the X-ray coordinate system of a treatment position 40 specified on the ultrasonic image and the coordinates of the isocenter 30, thereby calculating the angle of the calculated straight line 50.

With reference to FIG. 6 again, the angle control unit 121c controls the arm so that the subject is radiographed at the angle calculated by the calculating unit 121b. Specifically, the angle control unit 121c controls the C-arm and table system control unit 119 to control the C-arm 115 so that the straight line connecting the X-ray tube 112 and the X-ray detector 116 and the angle match the calculated straight line and angle, respectively. For example, the angle control unit 121c controls the C-arm and table system control unit 119 so as to position the X-ray tube 112 and the X-ray detector 116 on both ends of the straight line 50 illustrated in FIG. 8.

Figure 9A:
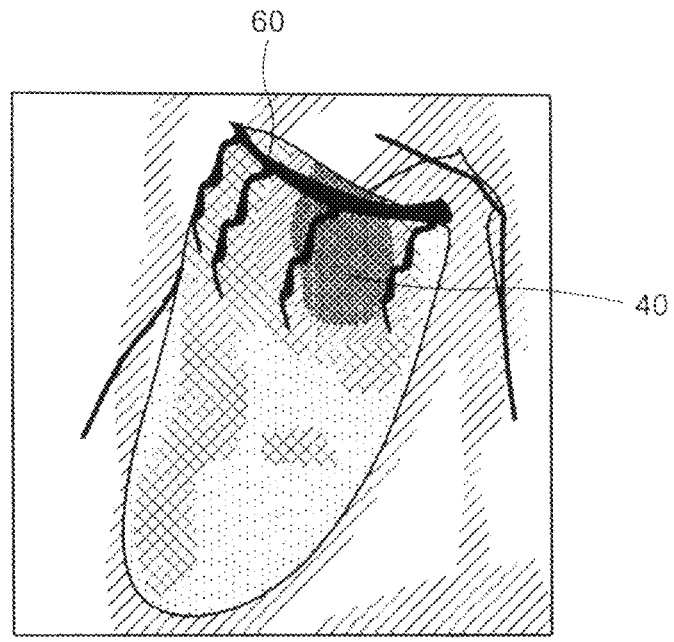
FIG. 9A is a diagram illustrating an example of a fused image adopting an X-ray image obtained through radiography from an angle controlled by an angle control unit according to the first embodiment.

FIG. 9A is a diagram illustrating an example of a fused image adopting an X-ray image obtained through radiography from an angle controlled by the angle control unit 121c according to the first embodiment. For example, a fused image adopting an X-ray image obtained through radiography by the C-arm 115 controlled by the angle control unit 121c is, as illustrated in FIG. 9A, the image in which a site of latest activation 40 superimposed onto the ultrasonic image can be observed from an anterior view. The fused image therefore enables the observer to clearly understand the positional relation between a blood vessel 60 that is enhanced in the X-ray image and the site of latest activation 40. This achieves placing an electrode in a precise manner in the CRT, for example.

Figure 9B:
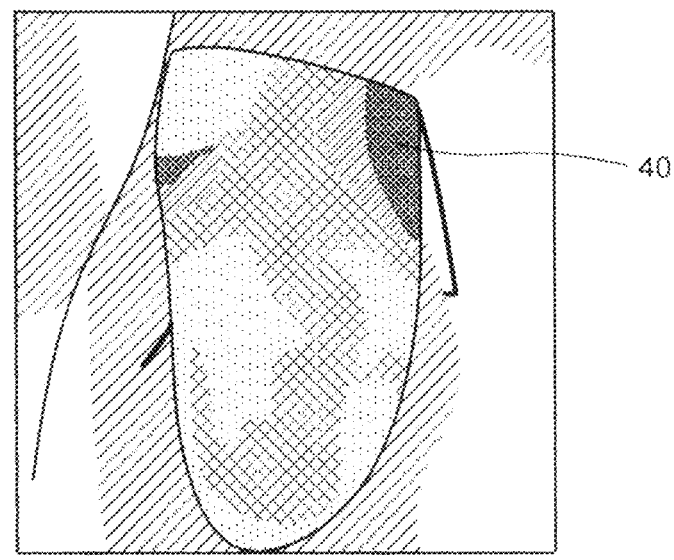
FIG. 9B is a diagram illustrating an example of a fused image adopting an X-ray image obtained through radiography without control by the angle control unit according to the first embodiment.

If the radiography is not under the control of the system control unit 121 according to the present embodiment, the site of latest activation cannot be observed from an anterior view. This may result in reduction of the visibility of the fused image. FIG. 9B is a diagram illustrating an example of a fused image adopting an X-ray image obtained through radiography without control by the angle control unit 121c according to the first embodiment.

For example, in the fused image adopting an X-ray image obtained through radiography without control by the angle control unit 121c according to the first embodiment, as illustrated in FIG. 9B, the site of latest activation 40 exists on the side of the target image. The observer therefore cannot clearly understand the positional relation between the blood vessel 60 that is enhanced in the X-ray image and the site of latest activation 40.

As described above, the system control unit 121 according to the first embodiment obtains X-ray image through radiography at the angle of the straight line connecting the site of latest activation (the treatment position) and the isocenter and generates a fused image. This achieves displaying a fused image in which the site of latest activation (the treatment position) can be observed from an anterior view. This achieves suppressing the reduction of the visibility of the superimposed image.

During observation of the fused image relating to placing an electrode in the CRT, for example, the position of the table 114 may be changed. On this occasion, the positional relation between the X-ray coordinate system and the ultrasound coordinate system changes. The X-ray diagnosis apparatus 100 according to the first embodiment updates the angle of the C-arm when the positional relation between the X-ray coordinate system and the ultrasound coordinate system changes.

In the above-described example, the calculating unit 121b corrects the coordinates in the X-ray coordinate system by using the travel distance of the table 114, thereby updating the positional relation between the X-ray coordinate system and the ultrasound coordinate system and updating the angle of the C-arm. FIG. 10 is a diagram for explaining an example of update processing of the angle performed by the calculating unit 121b according to the first embodiment.

For example, as illustrated in FIG. 10 (A), when the angle between the treatment position and the isocenter is calculated with the center of the X-ray coordinate system determined as the isocenter, and if the table 114 is moved, the calculating unit 121b moves the X-ray coordinate system based on the travel distance of the table 114 as illustrated in FIG. 10 (B). The calculating unit 121b calculates the angle between the isocenter and the treatment position in the X-ray coordinate system after the movement and updates the angle with the calculated angle.

Figure 11:
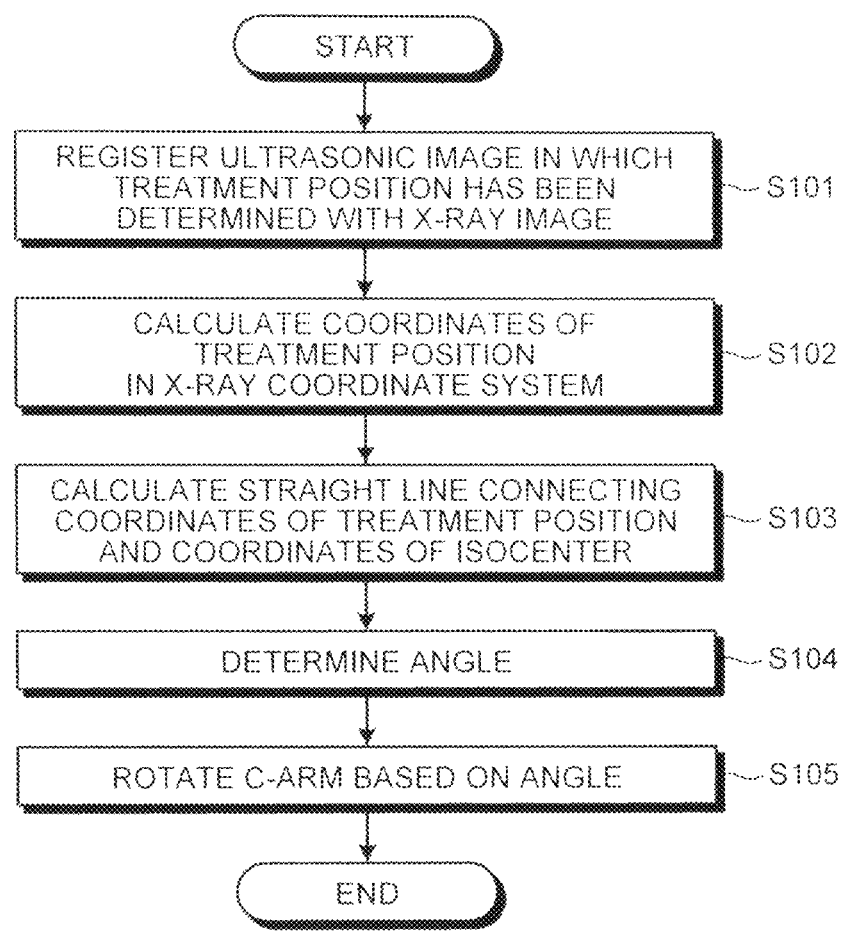
FIG. 11 is a flowchart illustrating procedures for processing performed by the X-ray diagnosis apparatus according to the first embodiment.

The following describes procedures for processing performed by the X-ray diagnosis apparatus 100 according to the first embodiment. FIG. 11 is a flowchart illustrating procedures for processing performed by the X-ray diagnosis apparatus 100 according to the first embodiment. FIG. 11 illustrates the processing after the X-ray diagnosis apparatus 100 acquires the ultrasonic image.

As illustrated in FIG. 11, in the X-ray diagnosis apparatus 100 according to the first embodiment, the positioning unit 121a registers the ultrasonic image in which the treatment position has been determined with the X-ray image (Step S101). The calculating unit 121b then calculates the coordinates of the treatment position in the X-ray coordinate system from the X-ray coordinate system and the ultrasound coordinate system registered with each other by the positioning unit 121a (Step S102).

After that, the calculating unit 121b calculates the straight line connecting the calculated coordinates of the treatment position and the coordinates of the isocenter (Step S103), and determines the angle of the C-arm (Step S104). The angle control unit 121c rotates the C-arm based on the determined angle (Step S105), and the processing ends.

As described above, according to the first embodiment, the calculating unit 121b calculates the angle between the treatment position specified in the ultrasonic image generated through transmission and reception of ultrasonic waves by the ultrasound probe and the position of the isocenter in the radiographic space based on the information on the relative position between the radiographic space where a subject is radiographed and the scanning space where the subject is scanned by the ultrasound probe 320. The angle control unit 121c controls the C-arm 115 so that the subject is radiographed at the angle calculated by the calculating unit 121b. This enables the X-ray diagnosis apparatus 100 according to the first embodiment to display a fused image in which the treatment position can be observed from an anterior view. This achieves suppressing the reduction of the visibility of the superimposed image.

According to the first embodiment, the calculating unit 121b determines the center of the radiographic space as the isocenter. This enables the X-ray diagnosis apparatus 100 according to the first embodiment to readily calculate the angle between the treatment position and the isocenter.

According to the first embodiment, the calculating unit 121b calculates the intersection point of the centers of images in X-ray images obtained through radiography in the radiographic space and determines the calculated intersection point as the isocenter. This enables the X-ray diagnosis apparatus 100 according to the first embodiment to readily determine the position of the isocenter.

In the above-described first embodiment, the intersection point of the respective center of X-ray images is determined as the isocenter. In the second embodiment, the position of the isocenter is moved to the center of the heart. That is, in the X-ray diagnosis apparatus 100 according to the second embodiment, the coordinates of the isocenter is extracted from a plurality of X-ray images, and the C-arm and the table 114 are moved so that the center of the heart is located on the extracted coordinates.

The calculating unit 121b according to the second embodiment calculates the positional relation between the center of the heart in the ultrasonic image and the isocenter. Specifically, the calculating unit 121*b* acquires the coordinates of the center of the heart in the ultrasound coordinate system based on the information on a ventricle acquired by the ultrasound diagnosis apparatus 300. The calculating unit 121*b* calculates the travel distance based on the acquired coordinates so that the isocenter matches the center of the heart. The information on a ventricle acquired by the ultrasound diagnosis apparatus 300 is, for example, an apical four-chamber view. The calculating unit 121*b* acquires the center of the apical four-chamber view (e.g., the gravity point) as the center of the heart. The cross-sectional view used herein is not limited to the apical four-chamber view, and other apical chamber views or a subcostal view may be used. The center of the heart may be determined as the center of the short axis of the heart included in an image representing the treatment position.

FIG. 12 is a diagram for explaining an example of processing performed by the calculating unit 121*b* according to the second embodiment. For example, as illustrated in FIG. 12 (A), the calculating unit 121*b* acquires the coordinates of the center of the heart in the ultrasound coordinate system and calculates the coordinates of the center of the heart in the X-ray coordinate system. The calculating unit 121*b* calculates the travel distance from the coordinates of the isocenter to the coordinates of the center of the heart in the X-ray coordinate system. That is, as illustrated in FIG. 12 (B), the calculating unit 121*b* calculates the travel distance used for superimposing the coordinates of the isocenter and the coordinates of the center of the heart.

The angle control unit 121*c* according to the second embodiment controls at least one of the C-arm 115 and the table 114 based on the positional relation calculated by the calculating unit 121*b* so that the center of the heart is positioned almost the same as the isocenter. Specifically, the angle control unit 121*c* moves at least one of the C-arm 115 and the table 114 by the travel distance calculated by the calculating unit 121*b*.

The following describes procedures for processing performed by the X-ray diagnosis apparatus 100 according to the second embodiment. FIG. 13 is a flowchart illustrating procedures for processing performed by the X-ray diagnosis apparatus 100 according to the second embodiment. FIG. 13 illustrates the processing after the X-ray diagnosis apparatus 100 acquires the ultrasonic image.

As illustrated in FIG. 13, in the X-ray diagnosis apparatus 100 according to the second embodiment, the positioning unit 121*a* registers the ultrasonic image in which the treatment position has been determined with the X-ray image (Step S201). The calculating unit 121*b* calculates the travel distance based on the positional relation between the center of the heart and the isocenter so that the isocenter matches the center of the heart (Step S202). The angle control unit 121*c* moves at least one of the C-arm 115 and the table 114 by the calculated travel distance, thereby moving the coordinates so that the isocenter matches the center of the heart (Step S203).

After that, the calculating unit 121*b* calculates the coordinates of the treatment position in the X-ray coordinate system based on the X-ray coordinate system and the ultrasound coordinate system registered with each other by the positioning unit 121*a* (Step S204). After that, the calculating unit 121*b* calculates the straight line connecting the calculated coordinates of the treatment position and the coordinates of the isocenter (Step S205) and determines the angle of the C-arm (Step S206). The angle control unit 121*c* rotates the C-arm based on the determined angle (Step S207), and the processing ends.

As described above, according to the second embodiment, the calculating unit 121*b* calculates the positional relation between the center of the heart included in the ultrasonic image and the isocenter. The angle control unit 121*c* controls at least one of the C-arm 115 and the table 114 based on the positional relation calculated by the calculating unit 121*b* so that the center of the heart is positioned almost the same as the isocenter. This enables the X-ray diagnosis apparatus 100 according to the second embodiment to always display a fused image as an image in a direction inwards from the wall of the heart. This achieves suppressing the reduction of the visibility of the superimposed image.

For example, if the isocenter is positioned almost the same as or in the vicinity of the treatment position (e.g., in the same plane), the fused image may be displayed in the direction parallel to the cardiac muscles rather than the direction perpendicular to the cardiac muscles. In the X-ray diagnosis apparatus 100 according to the second embodiment, this situation is avoided and the fused image can be always displayed in the direction perpendicular to the cardiac muscles (the direction inwards from the wall of the heart). In other words, the X-ray diagnosis apparatus 100 according to the second embodiment always achieves observation of cardiac muscles on a large plane.

In the above-described first and second embodiments, the angle between the treatment position and the isocenter has been calculated. In the third embodiment, the angle between the treatment position and the center of the heart is calculated.

The calculating unit 121*b* according to the third embodiment calculates the treatment position in the X-ray coordinate system and the position of the center of the heart. Specifically, the calculating unit 121*b* calculates the coordinates of the treatment position in the X-ray coordinate system from the X-ray image and the ultrasonic image registered with each other by the positioning unit 121*a*. The calculating unit 121*b* acquires the coordinates of the center of the heart in the ultrasound coordinate system and calculates the coordinates of the center of the heart in the X-ray coordinate system. The calculating unit 121*b* calculates the straight line connecting the calculated coordinates of the treatment position and the coordinates of the center of the heart, thereby calculating the angle of the calculated straight line.

The angle control unit 121*c* according to the third embodiment controls the arm so that the subject is radiographed at the angle calculated by the calculating unit 121*b*. Specifically, the angle control unit 121*c* controls the C-arm and table system control unit 119 to control the C-arm 115 so that the straight line connecting the X-ray tube 112 and the X-ray detector 116 and the angle match the calculated straight line and the angle respectively.

The following describes procedures for processing performed by the X-ray diagnosis apparatus 100 according to the third embodiment. FIG. 14 is a flowchart illustrating procedures for processing performed by the X-ray diagnosis apparatus 100 according to the third embodiment. FIG. 14 illustrates the processing after the X-ray diagnosis apparatus 100 acquires the ultrasonic image.

As illustrated in FIG. 14, in the X-ray diagnosis apparatus 100 according to the third embodiment, the positioning unit 121*a* registers the ultrasonic image in which the treatment position has been determined with the X-ray image (Step S301). The calculating unit 121*b* then calculates the coordinates of the treatment position in the X-ray coordinate system from the X-ray coordinate system and the ultrasound coordinate system registered with each other by the positioning unit 121*a* (Step S302). The calculating unit 121*b* calculates the coordinates of the center of the heart in the X-ray coordinate system (Step S303).

After that, the calculating unit 121*b* calculates the straight line connecting the calculated coordinates of the treatment position and the coordinates of the center of the heart (Step S304) and determines the angle of the C-arm (Step S305). The angle control unit 121*c* rotates the C-arm based on the determined angle (Step S306), and the processing ends.

As described above, the calculating unit 121*b* according to the third embodiment calculates the angle between the coordinates of the treatment position (specified position) and the coordinates of the center of the heart with the center of the heart determined as a predetermined position. The angle control unit 121*c* controls the C-arm so that the subject is radiographed at the angle calculated by the calculating unit 121*b*. This enables the X-ray diagnosis apparatus 100 according to the third embodiment to display a fused image in which the treatment position can be always observed from an anterior view regardless of the position of the isocenter.

According to an image processing apparatus according to at least one of the embodiments described above, the reduction of the visibility of a superimposed image of the X-ray image and the ultrasonic image can be suppressed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
   a table configured to mount a subject;
   an arm holding an X-ray tube for radiographing the subject on the table; and
   processing circuitry configured to
      acquire an X-ray image of the subject by controlling the X-ray tube and the arm;
      collect an ultrasonic image acquired in a state where the subject is placed on the table;
      identify a relative position between a radiographic space where the X-ray image was acquired and a scanning space where the ultrasonic image was acquired, by performing registration between the X-ray image and the ultrasonic image based on a position of a landmark set in the ultrasonic image and a position corresponding to the landmark in the X-ray image;
      calculate a straight line from a specified position specified in the ultrasonic image to an isocenter of the radiographic space based on the relative position between the radiographic space and the scanning space; and
      control the arm to move so that the subject is radiographed along the calculated straight line.

2. The X-ray diagnosis apparatus according to claim 1, wherein the processing circuitry is further configured to determine a center of the radiographic space as the isocenter.

3. The X-ray diagnosis apparatus according to claim 1, wherein the processing circuitry is further configured to calculate an intersection point of centers of images in a plurality of X-ray images obtained through radiography in the radiographic space, and determine the calculated intersection point as the isocenter.

4. The X-ray diagnosis apparatus according to claim 2, wherein the processing circuitry is further configured to
   calculate a positional relation between a center of a heart included in the ultrasonic image and the isocenter, and
   control at least one of the arm and a table based on the calculated positional relation so that the center of the heart is positioned almost the same as the isocenter.

5. An arm control method performed by an X-ray diagnosis apparatus, the arm control method comprising:
   acquiring an X-ray image of the subject on the table by controlling an X-ray tube held on the arm and controlling the arm;
   collecting an ultrasonic image acquired in a state where the subject is placed on the table;
   identifying a relative position between a radiographic space where the X-ray image was acquired and a scanning space where the ultrasonic image was acquired, by performing registration between the X-ray image and the ultrasonic image based on a position of a landmark set in the ultrasonic image and a position corresponding to the landmark in the X-ray image;
   calculating a straight line from a specified position specified in the ultrasonic image to an isocenter of the radiographic space based on the relative position between the radiographic space and the scanning space; and
   controlling the arm to move so that the subject is radiographed along the calculated straight line.

6. The arm control method according to claim 5, further comprising:
   determining a center of the radiographic space as the isocenter.

7. The arm control method according to claim 5, further comprising:
   calculating an intersection point of centers of images in a plurality of X-ray images obtained through radiography in the radiographic space, and
   determining the calculated intersection point as the isocenter.

8. The arm control method according to claim 6, further comprising:
   calculating a positional relation between a center of a heart included in the ultrasonic image and the isocenter, and
   controlling at least one of the arm and a table based on the calculated positional relation so that the center of the heart is positioned almost the same as the isocenter.

9. An arm control method performed by an X-ray diagnosis apparatus, the arm control method comprising:
   acquiring an X-ray image of the subject on the table by controlling the arm and an X-ray tube held on the arm;
   collecting an ultrasonic image acquired in a state where the subject is placed on the table;
   collecting a CT image of the subject acquired in advance;
   locating a scanning space where the ultrasonic image was acquired in a CT imaging space where the CT image was acquired, by performing registration between the ultrasonic image and the CT image;
   locating a radiographic space where the X-ray image was acquired in the CT imaging space, by performing registration between the X-ray image and the CT image;

identifying a relative position between the radiographic space and the scanning space, based on the position of the scanning space in the CT imaging space and the position of the radiographic space in the CT imaging space;

calculating a corresponding position in the radiographic space corresponding to a specified position specified in the ultrasonic image based on the relative position between the radiographic space and the scanning space;

calculating a straight line from the corresponding position to an isocenter of the radiographic space; and controlling the arm to move so that the subject is radiographed along the calculated straight line.

10. The arm control method according to claim 9, further comprising:

determining a center of the radiographic space as the isocenter.

11. The arm control method according to claim 9, further comprising:

calculating an intersection point of centers of images in a plurality of X-ray images obtained through radiography in the radiographic space, and determining the calculated intersection point as the isocenter.

12. The arm control method according to claim 10, further comprising:

calculating a positional relation between center of a heart included in the ultrasonic image and the isocenter, and controlling at least one of the arm and a table based on the calculated positional relation so that the center of the heart is positioned almost the same as the isocenter.

* * * * *